United States Patent [19]

Miyai et al.

[11] Patent Number: 5,922,544
[45] Date of Patent: Jul. 13, 1999

[54] METHOD OF CELL DETECTION

[75] Inventors: Kiyoshi Miyai, Minoo; Tsutomu Naitoh; Toshihiro Yonekawa, both of Otawara, all of Japan

[73] Assignee: Eiken Kagaku Kabushiki Kaish

[21] Appl. No.: 08/849,701

[22] PCT Filed: Dec. 27, 1995

[86] PCT No.: PCT/JP95/02734

§ 371 Date: Feb. 9, 1998

§ 102(e) Date: Feb. 9, 1998

[87] PCT Pub. No.: WO96/21041

PCT Pub. Date: Jul. 11, 1996

Related U.S. Application Data

[30] Foreign Application Priority Data

Dec. 29, 1994 [JP] Japan ............................... 6-338657

[51] Int. Cl.⁶ ............................. C12Q 1/68; C12P 19/34
[52] U.S. Cl. ................................. 435/6; 435/91.2
[58] Field of Search .............................. 435/6, 91.2, 7.1, 435/7.23; 536/23.1, 24.1

[56] References Cited

U.S. PATENT DOCUMENTS

| | | | |
|---|---|---|---|
| 4,358,537 | 11/1982 | Falkow et al. | 435/5 |
| 5,382,521 | 1/1995 | Raz et al. | 435/7.23 |
| 5,693,484 | 12/1997 | Nakamoto et al. | 435/39 |

FOREIGN PATENT DOCUMENTS 0 281 927   9/1988   European Pat. Off. .

OTHER PUBLICATIONS

Denninger et al. J. Mol. Biol. 151:17–33, 1981.

*Primary Examiner*—Eggerton A. Campbell
*Attorney, Agent, or Firm*—Knobbe, Martens, Olson & Bear, LLP

[57] ABSTRACT

A method and a reagent for detecting cells of a living organism contained in various samples of the organism by detecting genes specific for each animal species. This method is useful for detecting bleeding into feces. It is possible for confirming the bleeding of the human body to use an Alu sequence as the sequence specific for the animal species. As genes are used as the indicator in this method, fecal occult blood can be detected more specifically at a higher sensitivity than by the conventional technique using hemoglobin as the indicator.

8 Claims, 4 Drawing Sheets

Figure 1

SEQ ID NO 1 <BLUR8>

```
     TGTAAT CCGAGCACTT TGGGAGGCCA AGGAGGGCAG ATCACCTGAA  -101
GTCAGGAGTT TGAGACCAGC CTGGCCAACA TGGTGAAACT CCATCTCTAC  -51
TGAAAATACA AAAATTAGCC AGGCATGGTG ATGCGTGCCT GGAATCCCAG  -1
CTACTTAGGA GGCTGAGACA GAAGAATCCC TTAAACC. AA GAGGTGGAGG   49
TTGCAGTGAG CCGAGATCGC ACGGCTGCAC TCCAGCCT. G GTGACAGAGC   98
GAGACTCCAT CTCAAAAAAA A                                 119
```

Figure 2

SEQ ID NO 2 <BLUR1>

```
    CACAAAGG GCCATAAAAA TGTTCATAAT CTGGTGGGTG TGGTGGCTCA  -151
TGCCTGTAAT CCCAGCACTT TGGGAGGCCA AGGTGGGAGG ATGCCTTGAG  -101
TCTAGGAGTT TGAGAGATGC CTGGATAACA CAGAGAGACC CTCATCTCTA  -51
C. AAAA                                                 -49
```

Figure 3

SEQ ID NO 3 <BLUR2>

```
                              GCGGGGCG TGGTAGCTCA  -151
CACCTGTAAT CCCAATACTT TCGGAGGCTG AGGTGGGTGG ATAACTTGAC  -101
GTCAGGAGTT CAAGACCAGC TTGACCAACA TGGTGAAACC CCATCTCTAC  -51
TAAAAATACA AAAATTAGGC AGGGCTGGTG GCACGCACCT GTAACCCCAG  -1
CTACTCAGGA GGCTGAGGCA GGAGAATCAC TTGAACCCTA GAGGCAGAGG   50
TTGCAGTGAG CCGAGATCAT GCTACTGTAC . CCAGCCTGG GCAACAGAGT   99
GAGATTCCAT CTCAAAAAAA AAAAAAAGA AAAA                    134
```

Figure 4

SEQ ID NO 4 <BLUR6>

```
                                                  CGGTGGCTCA  -151
CACCTGTAAT CCCAGCACTT TGGGAGGCCA AGGTGGGCAG ATCACCTGAG  -101
CTCAGGAGTT TGAGACCAGC CTTGCCAACA TGGCAAAACC CCGTCTCTAT   -51
TAAAAATACA AAAATTAGCC GGGCAAGGAG GTGGGTGCCT GTAATCCCAG    -1
CTACTTGGGA GGCTGAGGCA GGAGAAACAC TTGAACCT..  ..........   38
...GGGAGAG CCGAGATAGT GCCACTGTAC TCCAGCCTGG GCAACAGAGT   85
GAGACTCTGT CA                                            97
```

Figure 5

SEQ ID NO 5 <BLUR7>

```
                 CTAACA CAGTGAAACC CTGTCTCTAC   -51
TAAAAATTCA AAAATTAGCC AGGCGTGGTG GCATGCGCCT GTAGTCCCAG    -1
CTACTTGGGA GGCTGAGGCA GGAGAATCGC TTGAACCCAG GAGATGGAGG   50
CTGCAGTGAG ACGAGATCCT GCCACCACAC TCCAGCCTGG GCAACAGAGC  100
AAGACTCCAT CTCAAAAAAC AAAAA                             125
```

Figure 6

SEQ ID NO 6 <BLUR10>

```
    AAAAAA AAAATTAGCC .GGCGTGGTG ACGGGCGCCT GTAGTCTCAG    -1
CTACTCAGGA GGCTGAGGCA GGAGAATGGC GTGAACCTGG GAGGTGGAGC   50
TTGCAGTGAG CCGAGATCGG GCCATTACAC TCCGGCCTGG GCGACAGAGC  100
GAGACTCCGT CTCAAAAAAA AAAAAAAAA AA                      132
```

Figure 7

SEQ ID NO 7 <BLUR11>

| | | | | | |
|---|---|---|---|---|---|
| TGTAATCC | CAGCACTTTT | GGGAGGCTGA | GGAGGGATGG | ATCACCTGAG | -101 |
| GTCAGGAGTT | CAAGACCAGC | CTGGCCAACA | TGGTGAAACC | CCGTTTCTAC | -51 |
| TAAAAATACA | AAAATTAGCT | GGGCATGGTG | GTGGGCACCT | GTAATCCCAG | -1 |
| CTACTCGGGA | GGCTGAGGCA | GGAGAATTGC | TTGAAACCAG | GAGGCAGAGG | 50 |
| TTGCAGTGAG | CTGAGATTGC | GCCACTGTAC | TTCAGGCTGT | GTGACAGAGT | 100 |
| GAGACTCCAT | CTCAAAAAAA | AAAAAAAAA | AA | | 132 |

Figure 8

SEQ ID NO 8 <BLUR13>

| | | | | | |
|---|---|---|---|---|---|
| | | TCCAGGGGA | GGGCTGGGCA | TGGTGGCTCA | -150 |
| CGTCCGTAAT | CCCAGCAGTT | TGGAAGGCTG | AGGCAAGTGG | ATCACTTTAA | -100 |
| GTCAGGAGTT | CAAGACCAGC | CTGGCCAACA | TGGCAAAACC | CCAACTCTAC | -50 |
| TAAAAACACA | A. AATTAGCC | GGGCGTGGTG | GCGCATGCCT | GTAGCCCCAG | -1 |
| CTACTCCTGA | GGCTGAGGCA | GGAGAATCGC | TTGAACCCGG | GAGGCAGATG | 50 |
| TTGCAGTGAG | CCGAGATCAC | ACCATTGCAC | TCCAGCCTGG | GCAACAAGAG | 100 |
| CGAAACTCCG | TCTCAAA | | | | 117 |

Figure 9

SEQ ID NO 9 <BLUR14>

| | | | | | |
|---|---|---|---|---|---|
| | | | | CAAGAG | -101 |
| GTCAGGAGTT | CAAAACCAAG | CTGGCTAACT | TGGTGAAACC | CTGTCTCTAC | -51 |
| TAAAAATACA | AAAATTAGCT | GGGCATGGTG | GTGCATGCCT | GTAATCCCAG | -1 |
| CTACTCGGGA | GGCTGAGGCG | AGAGAATTGC | TTGAACCCAG | GAGGTGGAGG | 50 |
| TTGCGATGAG | CCGAGATCGC | GCCACTGCAC | TCCAGCCTGG | GTGACAGTGC | 100 |
| AAAACTCTGT | CTAAAAAAAA | AAAAAGAAA | | | 129 |

Figure 10

SEQ ID NO 10 <BLUR19>

```
           CCCAACACTT TGGGAGGCCG AGGTAGATGG ATCACCTAAG  -99
GTCAGGACTT CAAAACCCAA CATGGCAAAA CACCA..TCA CTGCTTAAAA  -51
AAAGTAATAA AAAATTAGCC CAGTGTAATG ACACACACCT GTAGTCTCAG   -1
CTCTCCTGGA AGCTGAGGCA GGAGAATCGC TTGAACCCAG GAGGTGGAGG   50
TTACAGTGAG CCGAGATAGC GCCACTGCAC TCCAGCCTGA GCAACAGAGG  100
AAG                                                    103
```

Figure 11

Method of the Present Invention

METHOD OF CELL DETECTION

This application is a 371 of PCT/JP95/02734, filed on Dec. 27, 1995.

TECHNICAL FIELD

This invention relates to a method of detecting cells appearing in biological samples. A variety of cells are observed in the feces in cases of diseases of the digestive tract such as ulcers and tumors. For example, when there is bleeding into the feces, an observation of the blood cells in the feces can be an indicator of diseases in the digestive system. To be concrete, bleeding into the feces is often detected in cases of ulcers in the stomach and duodenum, or cancers in the digestive tract such as the esophagus, stomach, and colon. Except for regular bleeding, when diseases such as ulcerous colitis and tumorous necrosis cause a diapedesis, blood cells are observed in the feces.

It is especially important to detect occult blood in the feces when screening for colon cancer. To a certain degree, colon cancer can be detected in its early stages by taking a sample of the feces collected noninvasively. The diagnostic technology using bleeding into the feces as an indicator can also be applied to other animal species besides human beings.

In addition to feces, urine is commonly used as a biological sample. Detecting cells in urine is an important marker of disease. For example, urinary tract infection is suspected when white blood cells are detected in urine. Thus, the detection of cells in biological samples from a living organism, in which no cells can be detected under normal conditions, will provide valuable information for diagnosing many kinds of diseases.

BACKGROUND ART

Currently, a widely used method for detection of bleeding into feces is indexing hemoglobin derived from blood. Accordingly, a method of biochemical coloring reaction using hemoglobin's peroxidase-like activity, and a method of immunological detection using an antibody against hemoglobin (Songstar et al., Cancer. 45, pp. 1099–1102, 1980) are known. Even though the former biochemical method can detect blood from the digestive tract, there is always the possibility of a false-positive because a similar reaction may be caused by other substances with peroxidase-like activity or animal hemoglobin originating from diet. On the other hand, the latter immunological method will not be influenced by animal hemoglobin or substances with peroxidase-like activity originating from diet. The immunological method with those characteristics is widely used because testing can be done at any time without restricting meals.

Even though the immunological method of detecting fecal occult blood has been successful in terms of specificity and sensitivity, even now there are several problems raised about that method. The biggest problem is the hemoglobin's stability while it is in the digestive tract, and its stability at the time of preservation or transportation of the fecal samples. Feces contain several factors which will significantly affect the hemoglobin's immunological activity. In the case of bleeding in an upper part of the digestive tract, hemoglobin's detection sensitivity will be strongly influenced by digestion by digestive enzymes, the biological dissolution by microorganisms, or chemical transformation under acidic conditions. There are cases in which no hemoglobin is detected in spite of bleeding because the hemoglobin's immunological activity was weakened or lost due to a non-specific adhesion of various kinds of solid substances. Thus, bleeding detection techniques using hemoglobin as an indicator can detect bleeding in a lower part of the digestive tract. However, there is a stability problem when used as an indicator of bleeding in the upper part of the digestive tract. Furthermore, there is also a possibility of false negative detection due to unknown factors that cannot be explained simply by the above causes. The solutions to these problems are in great demand.

Another problem with the immunological method is to maintain specificity. The immunological method accomplishes a higher specificity, compared with the classical method using hemoglobin's chemical activity as an indicator. It also demands strict conditions of quality control for the reagent because its higher specificity strongly depends on the characteristics of antibodies.

As mentioned above, difficult problems still remain unsolved in the immunological method. They are: (1) an oversight of bleeding in the upper part of the digestive tract, (2) stability problems in preservation, neglect, and transportation of the samples; and (3) difficulty in reagent control. Therefore, there is a strong expectation of new technology which can easily accomplish superior specificity to the immunological method.

The other substances are tested as an indicator to solve the hemoglobin stability problem. For example, the trypsin inhibitor, $\alpha$1-anti-trypsin ($\alpha$1AT), has been used as an indicator for detecting bleeding into the feces. However, it was pointed out that $\alpha$1AT can be detected in feces due to causes other than bleeding. It is not widely used because its stability in the digestive tract or the feces was proved to be less than that of hemoglobin. On the other hand, genes have been used as an indicator for analysis of organisms. For example, Kourilsky and others disclosed a method for detection of nucleic acid with an enzyme labeled probe (U.S. Pat. No. 4581333). Ranki disclosed a sandwich hybridization assay method (U.S. Pat. No. 4489839). Those technologies are widely used for detecting nucleic acid of genetic composition, and they are applied to a variety of the samples. Many reports on the detection of genes related to cancers, viruses, and germs are presented. There is a report on an experiment to detect cancerous genes in feces with an application of this technology (Science 256; 102–05,1992).

DISCLOSURE OF INVENTION

A theme of the present invention is to propose a new marker, which can detect cells in feces. The new marker as a theme of this invention should have stability in the digestive tract and stability during transportation. Today, the immunological method is exclusively used for screening colon cancer, which is a diseases in the lower digestive tract, taking into consideration the hemoglobin's stability. This invention proposes a technology which is equal or more in terms of specificity to the current immunological detection technology using hemoglobin as an indicator of bleeding.

In addition to that, this invention provides a new idea that is expected to improve sensitivity, which is limited in the immunological method using hemoglobin as an indicator of bleeding.

Namely, this invention provides a method for detecting the existence or a trace of the existence of cells originated from an animal contained in various biological samples from the animal by detecting genes specific for said animal species. The cell detection method in the present invention is very useful, especially in its application to cell detection in feces. Furthermore, using this cell detection method, this invention provides technology for detecting fecal occult blood, and a new reagent useful for those detection methods.

DETAILED DESCRIPTION OF PREFERRED EMBODIMENTS

In the cell detection method of this invention, feces and urine are analyzed as biological samples. The animal cells are rarely observed in those biological samples under normal conditions. In many occasions, the appearance of cells of the living organism in those biological samples indicates an abnormal indicator. As an abnormal indicator, cells in the feces may indicate, for example, blood cells due to bleeding or diapedesis, and tissue cells due to damage to the digestive organ tissues. White blood cells in urine indicate an abnormal indicator. Those cells indicate an abnormal indicator, not only when they are detected as complete cells maintaining cell structure, but also when they are detected as traces of damaged cells. For example, cell structures are highly likely to be destroyed by digestive function in upper digestive tract such as the stomach.

Hybridization assay is a desirable technique for detecting genes in this invention. Hybridization assay is an analysis technology based on an affinity between nucleic acids with complementary sequences. Basically, nucleic acids in the samples are formed into a single strand through denaturation by heat operation and then probes with complement sequences react to intended sequences. Formation of a double strand proves the existence of target nucleic acids. By fixing nucleic acids to a nitrocellulose membrane (blotting) beforehand, and adding a labeled probe as reagent, formation of the double strand can be easily confirmed by checking the presence of labels on the membrane. Various analysis systems based on that reaction principle have been proposed so far. In the present invention, the gene sequence specific to the animal species is chosen as detecting subject, but once the specific sequence is chosen, any known analysis technologies can be adapted to detect the sequence in a biological sample. Genes including DNA and RNA are detectable. Various detection technologies for both subjects are known. It is preferable to use DNA as the detecting subject in order to achieve better stability.

The solid phase sandwich hybridization assay can be mentioned as an embodiment of analysis technology. This technology requires two complement probes for two physically separated areas on the genes of the detecting subject. One probe is fixed on the solid phase and the other reacts as a labeled probe. When there is a sequence to be detected, both of solid phase probe and labeled probe will hybridize to the gene to be detected, and then form a sandwich structure. Because this superior technology does not require blotting the detecting subject's genes on the membrane, it can be easily analyzed if only the reagent is provided.

The polymerase Chain Reaction (PCR) method can be mentioned as another applicable technology to analyze genes for this invention. The PCR method, based on the reaction principle wherein setting a sequence called primer as an extension point, after synthesizing a double strand extension from the primer using single strand nucleic acid as a template, the finished double strand is denatured into a single strand, and then repeats double strand synthesis.

In this analysis technology, the number of nucleic acids can be amplified logarithmically because a substance resulting from reaction can be used as a template in the next step.

When the PCR method is applied to this invention, gene sequences specific to animal species' cells are set up as a detecting subject, and then primers with complement sequences are provided at both the 3'end of gene sequence and the 3'end of the complement sequence thereof. With the PCR method, primers established in such a manner will amplify the genes specifically when targeted genes exist in the samples. Amplified genes can be confirmed as a single band after separating the reaction mixture with electrophoresis. The existence of amplification products can be detected with the aforementioned hybridization assay.

Prior to detecting genes, it is ideal to extract genes from the biological samples from the living organism. According to the principle of this invention, various substances contained in the feces of the biological samples from the living organism will not affect the analysis results at all. However, feces contain many kinds of substances like bacteria of the intestinal germs and food residue. It is desirable that handling of the feces is conducted in sanitary conditions because of the unpleasantness in handling feces. Feces can be easily used as analysis samples once it is dispersed into appropriate buffer solutions to become suspended, or once it is filtered with inactive filters that do not adhere to genetic composition, or supernatant is separated with a centrifugation.

It is convenient to use a currently marketed feces sampling container. A series of operations like quantitative collection of feces, suspension into buffer solution and filtering can be conducted in the same container. The feces sampling container is currently used to transport the samples for the immunological detection of hemoglobin because it can stand up to transportation (U.S. Pat. No. 5,149,506, U.S. Pat. No. 5,246,669, and U.S. Ser. No. 08/290,892 (1994)). These kinds of containers can be used without any modification in this invention. If there is some concern that gene's adhesion to the filters may affect detection sensitivity, the filters can be treated beforehand with inactive genes. The DNA in salmon sperm is commonly used for this purpose.

Transportation of the feces sample in the liquid form is not always necessary. For instance, a dried filter-paper smearing the feces can be transported in dry condition. In this case, it is necessary to extract and disperse gene elements from the filters before analysis. The extraction of gene elements can be done accurately and speedily with the use of microwave treatment and other methods.

It is recommended to use a variety of preservatives to protect the genes in feces because they may be damaged by micro-organisms and digestive enzymes during preservation. As effective preservatives, inhibitors for nucleic acid decomposition enzyme activity such as nuclease are a good example because genes are analysis substances. Specifically, various proteases, protein denaturant, and actin as inhibitors are useful.

Chelating agents such as EDTA and EGTA are effective preservatives because nuclease (DNase) needs divalent ions such as $Ca^{2+}$ and $Mg^{2+}$ in an activation process. The coexistence of unrelated nucleic acids (for example, salmon sperm DNA) is very effective for protecting nucleic acid because those unrelated nucleic acids will not cause a non-specific reaction. Besides preservatives, heat treatment of the samples at 80 to 100 degrees Celsius for about 5 minutes is an effective method to maintain stable preservation.

If there are concerns about preservative's negative effects on gene detection, preservatives are to be extracted, separated, or neutralized to prevent their negative effects before detection is conducted. For example, a possibility that a contamination of added protease into the analysis system may affect the nucleic acid amplification enzyme or the labeling enzyme is not negated. For those cases, it is advisable to add protease inhibitors or to conduct a heating operation for inactivation.

Occasionally, it is necessary to break down a cell for detection of the genes contained in the cell. It is possible for genes not to be completely detected without breaking down the cells when the cell structure is still maintained due to bleeding in the lower digestive tract. There are several well-known methods for extracting genes from cells. Those well-known gene extraction techniques are to be applied to this invention. For example, a combination of Proteinase K and sodium dodecyl sulfate (SDS) is a common method for gene extraction. Heating at 100 degrees Celsius for approximately 5 minutes will make gene extraction possible without an enzyme treatment.

In the above, when blood from upper digestive tract is the sole detection subject, a break-down process of blood cells is not necessary since the possibility that cell structures remain is low. By taking advantage of this feature in accordance with the cell detection method of the present invention, identification of the bleeding site can be expected to be presumed.

The gene detection processes of the present invention can be explained in detail by the following process in sequence, for example:

(1) Sample Preparation

This process is for forming single-strand genes by extracting genes with or without breaking down human cells contained in biological samples such as feces, followed by heat denaturation of the genes.

(2) Hybridization

This process is for hybridizing the thus-obtained single-strand genes and gene probes prepared in advance.

(3) Detection

The amount of the target genes is evaluated by determining the amount of either hybridized gene probes or non-hybridized gene probes after separating them.

Many variations of hybridization assay are known and can be adopted in the present invention. For PCR, the single-strand genes obtained in step (1) can be used as a template.

The present invention can be applied to various animals other than humans, such as cows, pigs, goats, dogs, cats, and so forth. By generating a gene sequence specific to the animal species to be tested to investigate bleeding, obtaining a probe based on the sequence, and checking whether or not a gene complementary to the probe is present in a sample such as feces, the target cells can be detected.

In the present invention, the genes specific to the animal species mean genes which are present in the animal species from which the cells to be detected are derived, and which cannot be detected in normal cells of other animal species, microorganisms which may be found in feces or biological material used as foods, or DNA sources which may be present in other substances of the sample. Thus, for example, sequences complimentary to genes, which may be present in gene sources of animal species other than the animal species to be tested, can be used as probes or primers in the present invention, if the genes having the sequences are not co-present with the analysis subject in the biological sample. These genes are included in the genes specific to the subject animal species in this invention.

In this invention, a gene called Alu sequence is to be used for detecting human cells. The Alu sequence is contained in every eukaryotic cell in the blood and the individual density per unit of blood fluctuates less, which makes stable and accurate bleeding analysis possible. Its existence in the blood, with a certain degree of consistent density, contributes to improved sensitivity. The Alu sequences exist as a repetitive sequence on a genome (one per 1,000 to 3,000 base pairs ) and approximately 400,000 or more Alu sequences are dispersed in a single cell. As a result, it is possible to detect a small quantity of cells with high sensitivity when an Alu sequence is used as an indicator.

A repetitive sequence comprising approximately 300 base pairs in a DNA chromosome of many eukaryotes is called an Alu sequence. A repetitive sequence in chromosomes is observed in many eukaryotes. In the case of human beings, it includes a restriction enzyme AluI recognition site (AGCT), as a part of the DNA sequence. The Alu sequence has a sequence structure unique to human beings. It is the ideal gene to be used for this invention. A nucleic acid sequence for a typical Alu sequence is shown in the sequence listing as listed as SEQ ID NOs:1–10. Those sequences are cloned by P. L. Deininger et al. as BLUR (Bam Linked Ubiquitous Repeat) 1 (SEQ ID NO:2), 2 (SEQ ID NO:3), 6 (SEQ ID NO:4), 7 (SEQ ID NO:5), 8 (SEQ ID NO:1), 10 (SEQ ID NO:6), 11 (SEQ ID NO:7), 13 (SEQ ID NO:8), 14 (SEQ ID NO:9), 19 (SEQ ID NO:10) (J. Mol. Bio.151,17–33;1981). Those sequences are stated with numbers in which 1 represents C in AGCT, the AluI recognition site, in FIG. 1–FIG. 10. Homology is easily compared by verifying each sequence, using the AluI recognition site as a yardstick (decision of consensus sequence). For this invention, the BLUR 8 (SEQ ID NO:1) is the best sequence among 10 sequences in the sequence table. SEQ ID NO:1 is one of the major sequences among the Alu sequences. Each of the 10 cloned sequences in the Deininger's report possesses, at least, more than 80% homology to SEQ ID NO:1. Therefore, in this invention, the ideal condition should be detectability of a sequence possessing more than 80% homology to the nucleic acid sequence of BLUR 8 indicated as SEQ ID NO: 1, which will lead to high sensitivity.

If an Alu sequence is chosen as the targeted gene, a whole gene or partial continuous sequence with 10–200 bases of genes are used as probes. An optimum hybridizing environment is to be established in accordance with a probe composed of the adopted nucleic acid sequences, taking into consideration stringency capable of maintaining specificity and sensitivity. A lower number of bases will cause specificity to fall. As mentioned before, it is an effective method to use a whole sequence shown specifically in SEQ ID NO:1 as a probe to detect a sequence with more than 80% homology. It is also possible to prepare plural synthetic probes if it is difficult to cope with a diversity of family species with a single probe. In any case, those methods are capable of an accurate analysis of a sequence with more than 80% homology mentioned above.

On the other hand, the Alu sequence comprises two different domains. One domain has an extremely high homology among individuals and the other one has an extremely high variation among individuals. A higher setting of stringency will rarely create any problems if a domain with a high homology is used as a probe. On the other hand, if the other domain with a high variation is selected as a probe, there will be a possibility of non-detection unless stringency capable of hybridizing accurately a sequence with a homology of more than 90%, ideally more than 80%, is provided. The Alu sequence is basically structured with sequences unique to human beings even if it contains a domain with a high variation. A necessary specificity can be maintained even if stringency is reduced a little.

On the other hand, when the PCR method is used for gene detection, continuous sequences are to be selected as primers, and they should be complement to the parts of 3' and 5' ends which are unique regions of the Alu sequence. A primer sequence is to be established, based on a similar standard as a probe. Bases in the 3' end should be completely complementary because they are a substrate for polymerase. The following sequences can be used as a primer and they are selected from SEQ ID NO:1 shown previously;
5'-GTAATCCGAG CACTTTGGGA GGC-3'
5'-ATTCTTCTGT CTCAGCCTCC-3'

The gene detection method in this invention is very useful for detecting bleeding from the digestive tract when feces are used as samples. Bleeding from the digestive tract provides important information to diagnose ulcers or tumors. Especially, fecal occult blood is considered an important diagnostic marker for screening of colon cancer. If urine is selected as the biological sample from the living organism for this invention, white blood cells will be detected in the urine. White blood cells in the urine is a marker of urinary tract infection.

This invention also provides a cell detection reagent made of a gene probe with sequences specific to the animal species. This reagent includes a gene probe required for the detection method mentioned above. As explained before, the Alu sequence is used as probe in this invention when a human cell is a detection object. The nucleic acid sequence in the Alu sequences, including SEQ ID NO:1 (BLUR8), is a typical sequence as a probe for human cell detection in this invention. Besides the Alu sequences, the beta-actin gene sequence is known as a unique human gene (Patent laid-open Hei7-99981 (filed: May 12, 1993) which claims priority based on U.S. patent application Ser. No. 061692).

The probe can be labeled with a marker substance if necessary. Radioisotopes, enzymes, luminescent materials, fluorescent materials and haptens are known as markers.

The reagent for detecting cells in this invention is composed of a variety of supplemental ingredients besides gene probes. It is a combination of ingredients for separating nucleic acid and a diluted solution of sample ingredients for marker detection and positive or negative control material to confirm analysis results. The enzyme reagents and the substrates are needed for a PCR method.

Genes specific to the animal species are an indicator of cells in this invention. The indicator can distinguish, at a high rate of accuracy, blood components due to diet from a trace of cells to be detected. In addition to that, it also accomplishes higher stability for samples during transportation, or for samples inside the digestive tract which is a very hostile environment for the preservation of samples. In this invention, genes can work as an indicator for cells in various biological samples from the living organism such as feces. Considering the backgrounds shown in the examples described later, human cells rarely appear in normal feces. The existence of the specific genes is useful evidence of the cells' existence. Strictly speaking, it is possible that the digestive organ's mucoid tissues are found in a healthy human being's feces, but a limited quantity of those tissues can be distinguished from abnormal conditions.

Genes like the Alu sequences exist in blood at a constant density. Indexing them for bleeding, results in stable accuracy of analysis because of a lower fluctuation of density in blood among individuals.

Choosing genes as an indicator for bleeding can improve specificity dramatically, and can amplify the detection object. Those special effects are not expected from currently used indicators. It is extremely useful to use the genes as an indicator for bleeding.

Hemoglobin is currently used as an indicator for bleeding. However, it cannot recognize accurately the animal species even though the immunological method is considered superior in terms of specificity. A high degree of manufacturing technology is necessary to acquire a superior antibody equipped with both specificity and reactivity. On the other hand, this invention, using genes as an indicator, can easily accomplish a superior specificity. An analysis technology based on gene sequencing can accomplish a higher specificity without using a special technology.

Furthermore, the use of genes is more advantageous in terms of stability. DNA is more stable in terms of degradation caused by acids, compared to protein such as hemoglobin. Also, they are rarely affected by a protein degradation enzyme, a digestive enzyme. The blood components in feces passed through the digestive tract are damaged by acids and protein degradation enzymes. There remains a possibility of degradation of the samples just before they are analyzed because they must be transported to a laboratory once they are collected. Accordingly, a gene's stability is a very significant characteristic to improve reliability of analysis results.

In addition to its stability, a gene's comparatively constant density in blood is an important attribute. It is possible for various components contained in blood to become an indicator for bleeding. If a component tends to fluctuate easily its density in blood among individuals is not an ideal indicator because of its lack of reliability. The Alu sequences showed in this invention are contained in every eukaryotic cell and its density in blood (approximately $20 \times 10^4$ cell/$\mu$l) is stable at a high level so as to maintain a high reliability as an indicator for bleeding.

EXAMPLES OF INVENTION

Example 1: Detection Sensitivity in Human DNA Detection System Using Alu Sequence Probe Heparin-added blood is gradually diluted with 200 μl physiological saline solution to make a sample. As another sample, the same quantity of blood was added to 200 μl solution suspended with 20 mg of a healthy human's feces, instead of physiological saline solution.

0.5% of SDS and 1 mg/ml Proteinase K (manufactured by Boehringer Mannheim) were added to both the physiological saline solution containing serial diluted heparin-added blood and the suspended solution with human feces (final concentration). After incubating for 30 minutes at 37 degrees Celsius, each of them was extracted once with ether. DNA collected in an ethanol precipitation process was air-dried and then dissolved into 100 μl distilled water.

This was dot-blotted on a nitrocellulose membrane according to the conventional method, an Alu sequence probe labeled with $^{32}P$ by the nick translation method was hybridized. DNA with basis sequence shown SEQ ID NO:1 was used as a probe. The result was evaluated after 18 hours of autoradiography. The result is shown in Table 1. Despite conjecture of a lower sensitivity and the effect of feces in the sample mixed with feces, it is confirmed that this invention's method can detect a 0.125 μl of blood per 20 mg of feces (about one scoop of a spatula).

TABLE 1

Detection Sensitivity in Human DNA Detection System Using Alu Sequence Probe

| Sample | | Outcome |
|---|---|---|
| Physiological Saline Solution 200 μl | | |
| + blood | 500 μl | 4+ |
| + blood | 125 μl | 4+ |
| + blood | 31.8 μl | 4+ |
| + blood | 7.8 μl | 3+ |
| + blood | 1.9 μl | 3+ |
| + blood | 0.5 μl | 2+ |
| + blood | 0.125 μl | 2+ |
| + blood | 0.031 μl | 1+ |
| + blood | 0.008 μl | − |
| + blood | 0 μl | − |
| Feces 20 mg/200 μl | | |
| + blood | 500 μl | 4+ |
| + blood | 125 μl | 4+ |
| + blood | 31.8 μl | 3+ |
| + blood | 7.8 μl | 3+ |
| + blood | 1.9 μl | 2+ |
| + blood | 0.5 μl | 2+ |
| + blood | 0.125 μl | + |
| + blood | 0.031 μl | ± |
| + blood | 0.008 μl | − |
| + blood | 0 μl | − |

Example 2: Examination of Specificity of Probes

The same detection procedures as in Example 1 were followed to confirm this invention's specificity, using cow and chicken blood instead of human blood. The orthotolidine method measuring kit, HEMATEST (brand name, Bayer), which is currently marketed for the detection of fecal occult blood, and the immunological latex agglutination method measuring kit, OC-HEMODIA EIKEN (Eiken Kagaku, brand name) were used for comparison. The operation was conducted according to the attached instructions. The orthotolidine method uses orthotolidine's color developing reaction caused by hemoglobin's peroxidase-like activity. On the other hand, the human hemoglobin is detected with the immunological latex agglutination method, which uses the agglutination reaction between human hemoglobin and polystyrene latex particles coated with anti-human hemoglobin antibody, when the human hemoglobin exists. The results are shown in Table 2. This invention proves that human blood can be distinguished clearly from the blood of chickens or cows, which may have mixed with food. Such animal blood is not distinguished by the orthotolidine method and shows exactly the same reaction as human blood.

The comparison was conducted among the conventional fecal occult blood detection methods such as the orthotolidine and latex agglutination methods and this invention's method. Feces samples collected after beef consumption were compared to feces samples collected after restricted meat consumption. The same procedures as in Example 1 were followed. The results are shown in Table 3. Both latex agglutination method and this invention's method recognized the animal species, indicating minus signs in all results. On the other hand, the orthotolidine method failed to recognize the animal species and indicated a false-positive sign which may caused by beef consumption.

TABLE 2

Specificity of Probes (Specificity to Animal Species)

| | |
|---|---|
| Healthy Human Feces (200 mg/200 μl) + human blood 1 μl | 2+ |
| + cow blood 1 μl | − |
| + chicken blood 1 μl | − |
| + no blood added | − |

TABLE 3

Specificity of Probes (Comparison with Conventional methods)

| | Present Invention | Orthotolidine Method | Latex Agglutination Method |
|---|---|---|---|
| Restricted Diet | − | − | − |
| Day 2 After Beef Ingestion | − | 2+ | − |
| Day 5 After Beef Ingestion | − | − | − |

Example 3: Comparison with Conventional Occult Blood Detection Methods

This invention's detection method was compared with conventional fecal occult blood methods such as the orthotolidine method (biochemical detection) and the latex agglutination method (immunological detection), using actual fecal samples. The same procedures were followed as in Example 1(this invention) or in Example 2 (conventional methods).

Each fecal sample was collected under no dietary restriction. The results are shown in Table 4. The ten samples consisted of positive samples of colon cancer screening test by latex agglutination test (samples 1–7), stomach ulcer patients' samples (samples 8–9), and a colon cancer patient's sample (sample 10). The results for sample 5 in the latex agglutination method (+→−; intermediate result between + and −) may have been caused by reduced hemoglobin antigenecity.

TABLE 4

Comparison with Conventional Occult Blood Detection Methods

| Samples | Present Invention | Orthotolidine Method | Latex Agglutination Method |
|---|---|---|---|
| 1 | 4+ | + | + |
| 2 | 4+ | + | + |
| 3 | 3+ | + | + |
| 4 | + | 2+ | + |
| 5 | + | + | + → − |
| 6 | + | + | + |
| 7 | 3+ | + | + |
| 8 | 2+ | 3+ | + |
| 9 | − | − | − |
| 10 | 3+ | 2+ | + |

Example 4: Detection Of Bleeding In Upper Digestive Tract

Using fecal samples collected from a healthy human being who ingested his own blood, this invention was compared with the conventional methods as a model of bleeding in the upper digestive tract. The comparison results between the present invention and the conventional methods of the orthotolidine method and latex agglutination method under the dietary restriction are shown in Table 5. The blood passed through the upper digestive tract could not be detected with the latex agglutination method. It may be due to a loss of hemoglobin antigenecity affected by stomach acids or various enzymes. On the other hand, this invention's method using DNA as an indicator could detect blood consistently.

TABLE 5

Detection of Bleeding in Upper Digestive Tract

| | Present Invention | Orthotolidine Method | Latex Agglutination Method |
|---|---|---|---|
| Restricted Diet After Oral Administration of Blood | − | − | − |
| Day 1 | + | − | − |
| Day 2 | + | 3+ | − |
| Day 3 | + | 2+ | − |
| Day 4 | + | 2+ | − |
| Day 7 | − | 2+ | − |

Example 5: Application To General Samples

Figure 1:
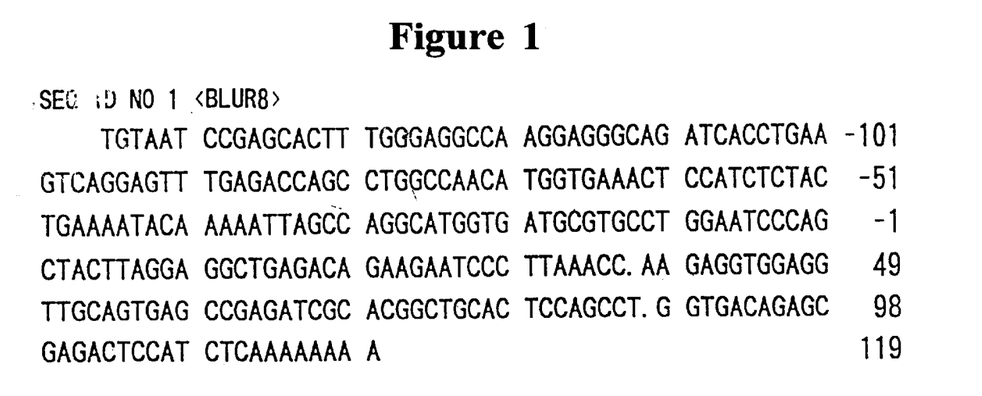
FIG. 1 is a sequence, in which C of AluI recognition region AGCT of BLUR 8 shown in SEQ ID NO:1 is numbered 1. In the figure, "." indicates deletion.
Figure 2:
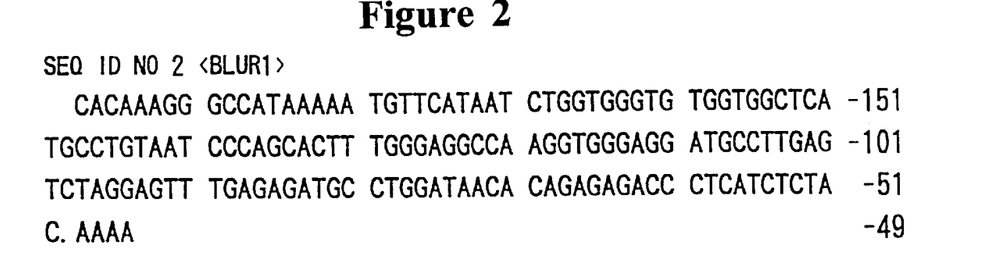
FIG. 2 is a sequence, in which C of AluI recognition region AGCT of BLUR 1 shown in SEQ ID NO:2 is numbered 1. In the figure, "." indicates deletion.
Figure 3:
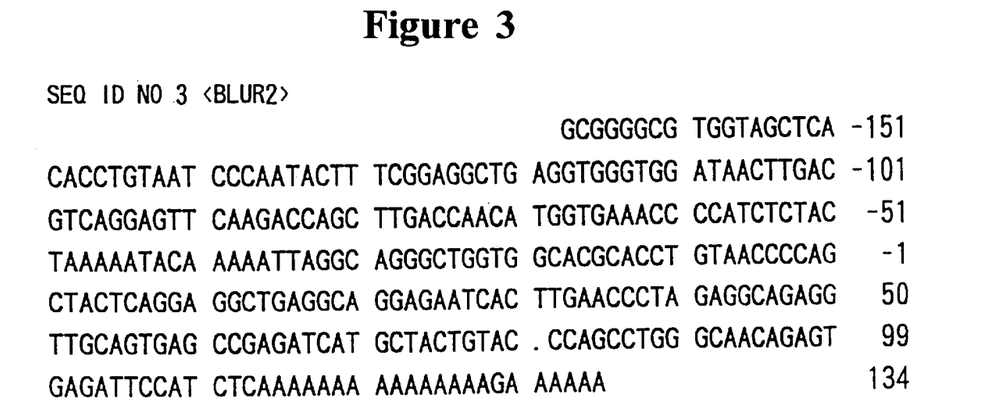
FIG. 3 is a sequence, in which C of AluI recognition region AGCT of BLUR 2 shown in SEQ ID NO:3 is numbered 1. In the figure, "." indicates deletion.
Figure 4:
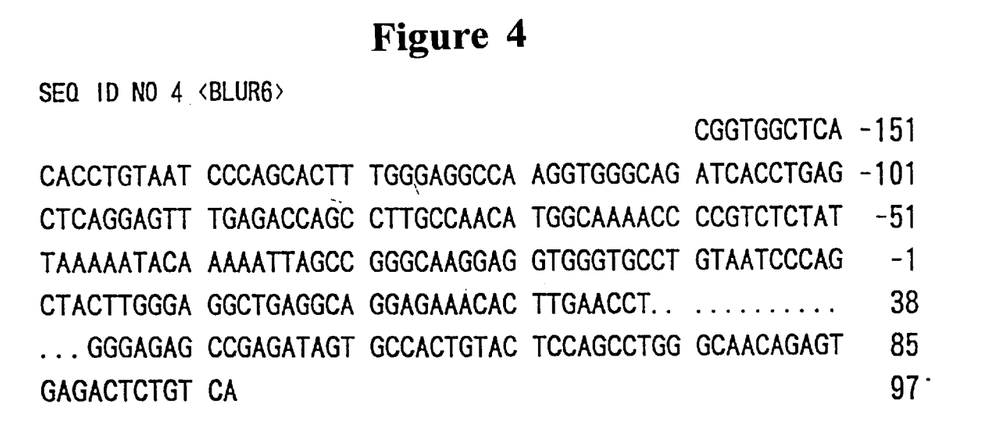
FIG. 4 is a sequence, in which C of AluI recognition region AGCT of BLUR 6 shown in SEQ ID NO:4 is numbered 1. In the figure, "." indicates deletion.
Figure 5:
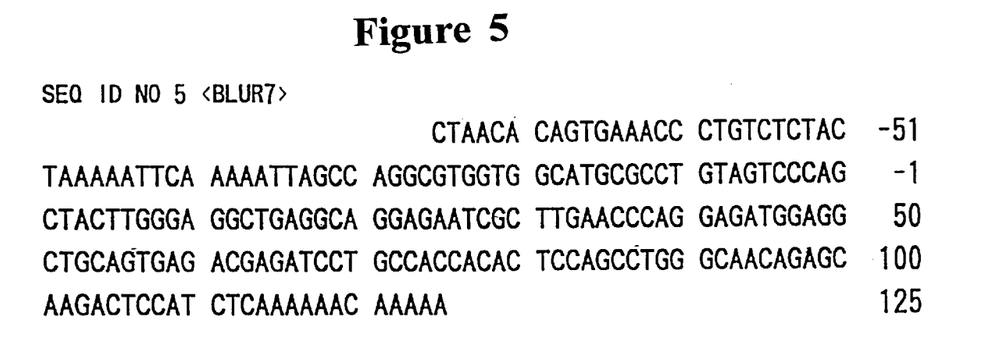
FIG. 5 is a sequence, in which C of AluI recognition region AGCT of BLUR 7 shown in SEQ ID NO:5 is numbered 1. In the figure, "." indicates deletion.
Figure 6:
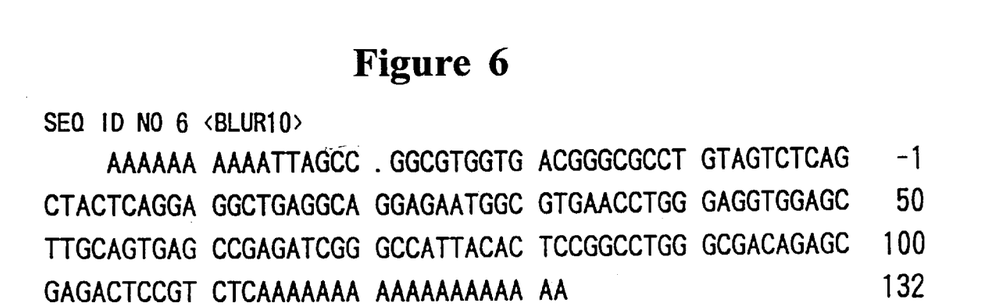
FIG. 6 is a sequence, in which C of AluI recognition region AGCT of BLUR 10 shown in SEQ ID NO:6 is numbered 1. In the figure, "." indicates deletion.
Figure 7:
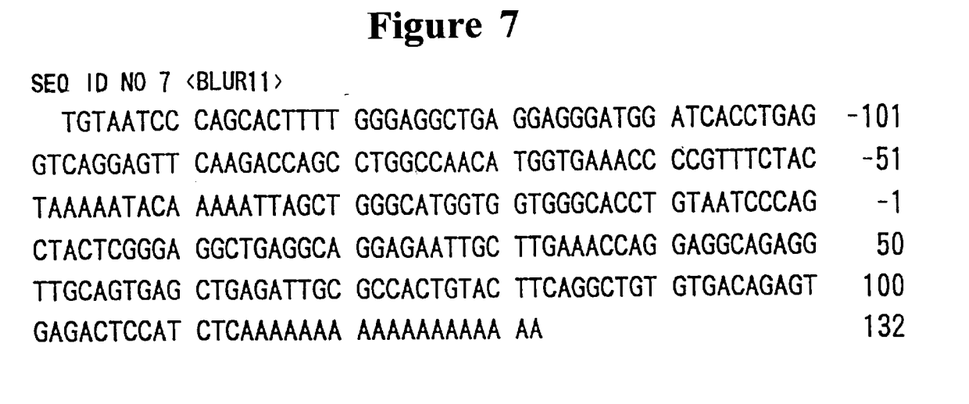
FIG. 7 is a sequence, in which C of AluI recognition region AGCT of BLUR 11 shown in SEQ ID NO:7 is numbered 1. In the figure, "." indicates deletion.
Figure 8:
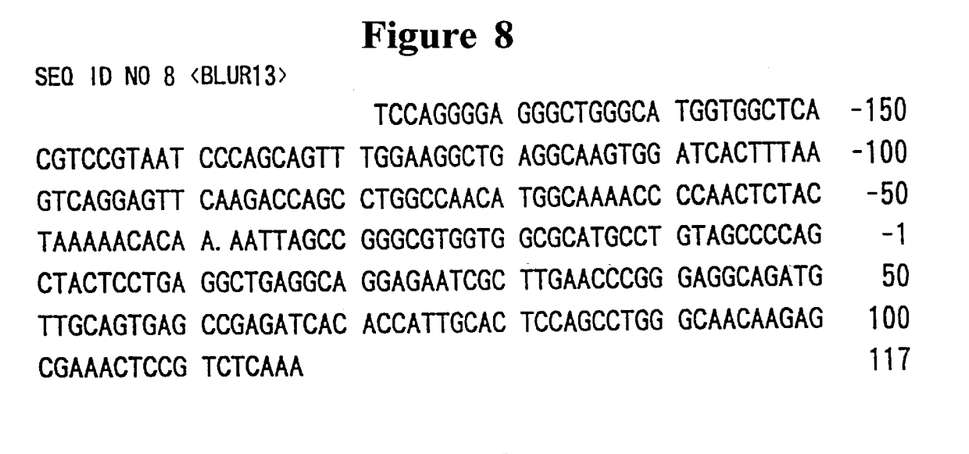
FIG. 8 is a sequence, in which C of AluI recognition region AGCT of BLUR 13 shown in SEQ ID NO:8 is numbered 1. In the figure, "." indicates deletion.
Figure 9:
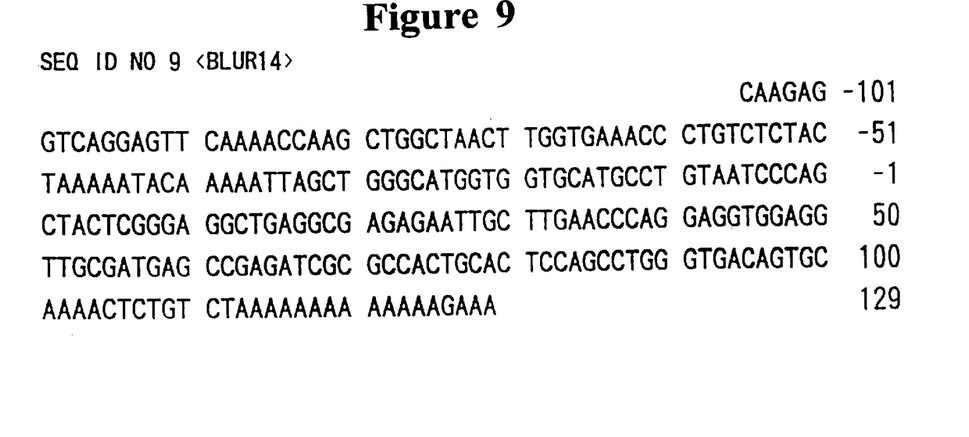
FIG. 9 is a sequence, in which C of AluI recognition region AGCT of BLUR 14 shown in SEQ ID NO:9 is numbered 1. In the figure, "." indicates deletion.
Figure 10:
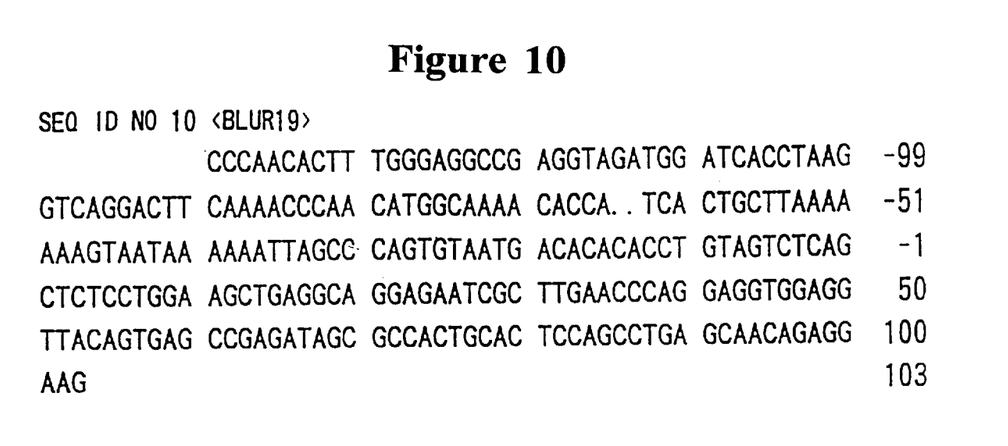
FIG. 10 is a sequence, in which C of AluI recognition region AGCT of BLUR 19 shown in SEQ ID NO:10 is numbered 1. In the figure, "." indicates deletion.
Figure 11:
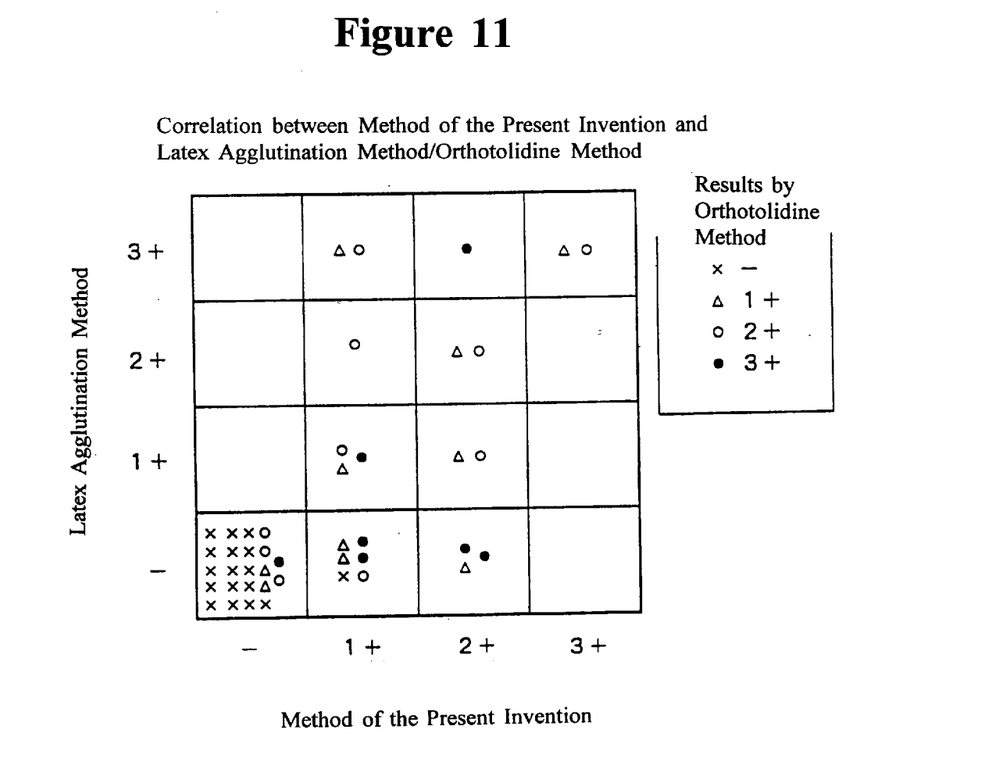
FIG. 11 shows a correlation between the results obtained by the blood detection method of the present invention and the results obtained by the conventional occult blood detection methods. In the figure, the results of the latex agglutination method, the present invention, and the orthotolidine method are indicated by the vertical axis, the horizontal axis, and the symbols in the figure, respectively. Each symbol means as follows: x;−, Δ;+, ○;2+, and ●;3+.

Using fecal samples collected for colon cancer screening, the measured results from both the conventional fecal occult blood detection method and the blood detection method using this invention were compared. Those feces were analyzed with the same procedures as in Example 1 (this invention) and Example 2 (conventional method), except for blood-added-feces. The results are shown in FIG. 11. It was confirmed that, in tests using actual fecal samples, this invention can detect fecal occult blood which cannot be detected with conventional orthotolidine and latex agglutination methods.

We claim:

1. A cell detection reagent for diagnosing abnormal conditions of a human by detecting a target polynucleotide contained in a biological sample from a living organism, said target polynucleotide specific to humans and present in normal cells, said reagent comprising:
   a gene probe having a nucleic acid sequence selected from the group consisting of the nucleic acid sequences listed as SEQ ID NOs:1–10, said probe hybridizing to the target polynucleotide;
   a solid support for immobilizing the target polynucleotide thereto; and
   a label for detecting the gene probe when binding to the target polynucleotide.

2. A cell detection reagent according to claim 1, wherein the nucleic acid sequence is SEQ ID NO:1.

3. A method for diagnosing abnormal conditions of a human associated with bleeding into feces or urine, comprising the steps of:
   sampling feces or urine from the human;

detecting the existence of a polynucleotide, if any, having an Alu sequence specific to humans and present in normal cells by using a probe having a nucleic acid sequence selected from the group consisting of the nucleic acid sequences listed as SEQ ID NOs:1–10, wherein the probe hybridizes to the polynucleotide; and correlating the existence of the detected polynucleotide with the abnormal conditions.

4. A method for diagnosing abnormal conditions according to claim 3, where the abnormal conditions are related to ulcers or cancers in the digestive tract.

5. The method for diagnosing abnormal conditions according to claim 3, further comprising the step of rupturing cells present in the feces or urine before the detection step, wherein bleeding into the upper and lower digestive tract is detected.

6. The method for diagnosing abnormal conditions according to claim 3, further comprising, prior to the correlating step, the step of comparing (a) the detected bleeding when the cell rupturing step is conducted, with (b) the detected bleeding when the cell rupturing step is not conducted, wherein the difference between (a) and (b) indicates bleeding into the lower digestive tract is detected.

7. The method for diagnosing abnormal conditions according to claim 3, wherein the probe has the nucleic acid sequence listed as SEQ ID NO:1.

8. The method for diagnosing abnormal conditions according to claim 3, wherein the probe consists of plural probes having different nucleic acid sequences selected from the group consisting of those listed as SEQ ID NOs:1–10.

* * * * *

```
                         SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 265 base pairs
         (B) TYPE: nucleic acid
         (C) STRANDEDNESS: double
         (D) TOPOLOGY: linear (ii) MOLECULE TYPE: Other (vii) IMMEDIATE SOURCE:
         (B) CLONE: Alu sequence BLUR8

(xi) SEQUENCE DESCRIPTION: SEQ ID NO:1:

TGTAATCCGA GCACTTTGGG AGGCCAAGGA GGGCAGATCA CCTGAAGTCA GGAGTTTGAG      60

ACCAGCCTGG CCAACATGGT GAAACTCCAT CTCTACTGAA AATACAAAAA TTAGCCAGGC     120

ATGGTGATGC GTGCCTGGAA TCCCAGCTAC TTAGGAGGCT GAGACAGAAG AATCCCTTAA     180

ACCAAGAGGT GGAGGTTGCA GTGAGCCGAG ATCGCACGGC TGCACTCCAG CCTGGTGACA     240

GAGCGAGACT CCATCTCAAA AAAAA                                          265

(2) INFORMATION FOR SEQ ID NO:2:

(i) SEQUENCE CHARACTERISTICS:
         (A) LENGTH: 153 base pairs
```

(B) TYPE: nucleic acid
        (C) STRANDEDNESS: double
        (D) TOPOLOGY: linear (vii) IMMEDIATE SOURCE:
        (B) CLONE: Alu sequence BLUR1

(xi) SEQUENCE DESCRIPTION: SEQ ID NO:2:

CACAAAGGGC CATAAAAATG TTCATAATCT GGTGGGTGTG GTGGCTCATG CCTGTAATCC         60

CAGCACTTTG GGAGGCCAAG GTGGGAGGAT GCCTTGAGTC TAGGAGTTTG AGAGATGCCT        120

GGATAACACA GAGAGACCCT CATCTCTACA AAA                                     153

(2) INFORMATION FOR SEQ ID NO:3:

(i) SEQUENCE CHARACTERISTICS:
        (A) LENGTH: 302 base pairs
        (B) TYPE: nucleic acid
        (C) STRANDEDNESS: double
        (D) TOPOLOGY: linear (vii) IMMEDIATE SOURCE:
        (B) CLONE: Alu sequence BLUR2

(xi) SEQUENCE DESCRIPTION: SEQ ID NO:3:

GCGGGGCGTG GTAGCTCACA CCTGTAATCC CAATACTTTC GGAGGCTGAG GTGGGTGGAT         60

AACTTGACGT CAGGAGTTCA AGACCAGCTT GACCAACATG GTGAAACCCC ATCTCTACTA        120

AAAATACAAA AATTAGGCAG GGCTGGTGGC ACGCACCTGT AACCCAGCT ACTCAGGAGG         180

CTGAGGCAGG AGAATCACTT GAACCCTAGA GGCAGAGGTT GCAGTGAGCC GAGATCATGC        240

TACTGTACCC AGCCTGGGCA ACAGAGTGAG ATTCCATCTC AAAAAAAAAA AAAAAGAAAA        300

AA                                                                      302

(2) INFORMATION FOR SEQ ID NO:4:

(i) SEQUENCE CHARACTERISTICS:
        (A) LENGTH: 257 base pairs
        (B) TYPE: nucleic acid
        (C) STRANDEDNESS: double
        (D) TOPOLOGY: linear (vii) IMMEDIATE SOURCE:
        (B) CLONE: Alu sequence BLUR6

(xi) SEQUENCE DESCRIPTION: SEQ ID NO:4:

CGGTGGCTCA CACCTGTAAT CCCAGCACTT TGGGAGGCCA AGGTGGGCAG ATCACCTGAG         60

CTCAGGAGTT TGAGACCAGC CTTGCCAACA TGGCAAAACC CCGTCTCTAT TAAAAATACA        120

AAAATTAGCC GGGCAAGGAG GTGGGTGCCT GTAATCCCAG CTACTTGGGA GGCTGAGGCA        180

GGAGAAACAC TTGAACCTGG GAGAGCCGAG ATAGTGCCAC TGTACTCCAG CCTGGGCAAC        240

AGAGTGAGAC TCTGTCA                                                      257

(2) INFORMATION FOR SEQ ID NO:5:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (vii) IMMEDIATE SOURCE:
        (B) CLONE: Alu sequence BLUR7

(xi) SEQUENCE DESCRIPTION: SEQ ID NO:5:

CTAACACAGT GAAACCCTGT CTCTACTAAA AATTCAAAAA TTAGCCAGGC GTGGTGGCAT         60

```
GCGCCTGTAG TCCCAGCTAC TTGGGAGGCT GAGGCAGGAG AATCGCTTGA ACCCAGGAGA        120

TGGAGGCTGC AGTGAGACGA GATCCTGCCA CCACACTCCA GCCTGGGCAA CAGAGCAAGA        180

CTCCATCTCA AAAAACAAAA A                                                  201

(2) INFORMATION FOR SEQ ID NO:6:

(i) SEQUENCE CHARACTERISTICS:
         (A) LENGTH: 177 base pairs
         (B) TYPE: nucleic acid
         (C) STRANDEDNESS: double
         (D) TOPOLOGY: linear (vii) IMMEDIATE SOURCE:
         (B) CLONE: Alu sequence BLUR10

(xi) SEQUENCE DESCRIPTION: SEQ ID NO:6:

AAAAAAAAAA TTAGCCGGCG TGGTGACGGG CGCCTGTAGT CTCAGCTACT CAGGAGGCTG         60

AGGCAGGAGA ATGGCGTGAA CCTGGGAGGT GGAGCTTGCA GTGAGCCGAG ATCGGGCCAT        120

TACACTCCGG CCTGGGCGAC AGAGCGAGAC TCCGTCTCAA AAAAAAAAAA AAAAAAA          177

(2) INFORMATION FOR SEQ ID NO:7:

(i) SEQUENCE CHARACTERISTICS:
         (A) LENGTH: 280 base pairs
         (B) TYPE: nucleic acid
         (C) STRANDEDNESS: double
         (D) TOPOLOGY: linear (vii) IMMEDIATE SOURCE:
         (B) CLONE: Alu sequence BLUR11

(xi) SEQUENCE DESCRIPTION: SEQ ID NO:7:

TGTAATCCCA GCACTTTTGG GAGGCTGAGG AGGGATGGAT CACCTGAGGT CAGGAGTTCA         60

AGACCAGCCT GGCCAACATG GTGAAACCCC GTTTCTACTA AAAATACAAA AATTAGCTGG       120

GCATGGTGGT GGGCACCTGT AATCCCAGCT ACTCGGGAGG CTGAGGCAGG AGAATTGCTT       180

GAAACCAGGA GGCAGAGGTT GCAGTGAGCT GAGATTGCGC CACTGTACTT CAGGCTGTGT       240

GACAGAGTGA GACTCCATCT CAAAAAAAAA AAAAAAAAA                              280

(2) INFORMATION FOR SEQ ID NO:8:

(i) SEQUENCE CHARACTERISTICS:
         (A) LENGTH: 295 base pairs
         (B) TYPE: nucleic acid
         (C) STRANDEDNESS: double
         (D) TOPOLOGY: linear (vii) IMMEDIATE SOURCE:
         (B) CLONE: Alu sequence BLUR13

(xi) SEQUENCE DESCRIPTION: SEQ ID NO:8:

TCCAGGGGAG GGCTGGGCAT GGTGGCTCAC GTCCGTAATC CCAGCAGTTT GGAAGGCTGA         60

GGCAAGTGGA TCACTTTAAG TCAGGAGTTC AAGACCAGCC TGGCCAACAT GGCAAAACCC       120

CAACTCTACT AAAAACACAA AATTAGCCGG GCGTGGTGGC GCATGCCTGT AGCCCCAGCT       180

ACTCCTGAGG CTGAGGCAGG AGAATCGCTT GAACCCGGGA GGCAGATGTT GCAGTGAGCC       240

GAGATCACAC CATTGCACTC CAGCCTGGGC AACAAGAGCG AAACTCCGTC TCAAA           295

(2) INFORMATION FOR SEQ ID NO:9:

(i) SEQUENCE CHARACTERISTICS:
         (A) LENGTH: 235 base pairs
```

(B) TYPE: nucleic acid
            (C) STRANDEDNESS: double
            (D) TOPOLOGY: linear (vii) IMMEDIATE SOURCE:
            (B) CLONE: Alu sequence BLUR14

(xi) SEQUENCE DESCRIPTION: SEQ ID NO:9:

CAAGAGGTCA GGAGTTCAAA ACCAAGCTGG CTAACTTGGT GAAACCCTGT CTCTACTAAA      60

AATACAAAAA TTAGCTGGGC ATGGTGGTGC ATGCCTGTAA TCCCAGCTAC TCGGGAGGCT     120

GAGGCGAGAG AATTGCTTGA ACCCAGGAGG TGGAGGTTGC GATGAGCCGA GATCGCGCCA     180

CTGCACTCCA GCCTGGGTGA CAGTGCAAAA CTCTGTCTAA AAAAAAAAAA AGAAA          235

(2) INFORMATION FOR SEQ ID NO:10:

(i) SEQUENCE CHARACTERISTICS:
            (A) LENGTH: 241 base pairs
            (B) TYPE: nucleic acid
            (C) STRANDEDNESS: double
            (D) TOPOLOGY: linear (vii) IMMEDIATE SOURCE:
            (B) CLONE: Alu sequence BLUR19

(xi) SEQUENCE DESCRIPTION: SEQ ID NO:10:

CCCAACACTT TGGGAGGCCG AGGTAGATGG ATCACCTAAG GTCAGGACTT CAAAACCCAA      60

CATGGCAAAA CACCATCACT GCTTAAAAAA AGTAATAAAA AATTAGCCCA GTGTAATGAC     120

ACACACCTGT AGTCTCAGCT CTCCTGGAAG CTGAGGCAGG AGAATCGCTT GAACCCAGGA     180

GGTGGAGGTT ACAGTGAGCC GAGATAGCGC CACTGCACTC CAGCCTGAGC AACAGAGGAA     240

G                                                                    241

(2) INFORMATION FOR SEQ ID NO:11:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:11:

GTAATCCGAG CACTTTGGGA GGC                                             23

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:12:

ATTCTTCTGT CTCAGCCTCC                                                 20